United States Patent
Swietoslawski et al.

(10) Patent No.: US 11,000,681 B2
(45) Date of Patent: May 11, 2021

(54) APPLICATOR FOR EXTERNAL ACTION FORMULATIONS, IN PARTICULAR A DISPOSABLE APPLICATOR FOR FORMULATIONS COMBATTING ECTOPARASITES

(71) Applicant: ICB PHARMA SPOLKA JAWNA, Jaworzno (PL)

(72) Inventors: Tomasz Swietoslawski, Jaworzno (PL); Pawel Swietoslawski, Jaworzno (PL)

(73) Assignee: ICB PHARMA SPOLKA JAWNA

( * ) Notice: Subject to any disclaimer, the term of this patent is extended or adjusted under 35 U.S.C. 154(b) by 648 days.

(21) Appl. No.: 15/514,560

(22) PCT Filed: Sep. 29, 2015

(86) PCT No.: PCT/IB2015/001700
§ 371 (c)(1),
(2) Date: Mar. 27, 2017

(87) PCT Pub. No.: WO2016/051248
PCT Pub. Date: Apr. 7, 2016

(65) Prior Publication Data
US 2017/0216570 A1    Aug. 3, 2017

(30) Foreign Application Priority Data
Sep. 29, 2014  (PL) .......................... 409627

(51) Int. Cl.
*A61M 35/00*  (2006.01)
*A61D 7/00*  (2006.01)

(52) U.S. Cl.
CPC .............. *A61M 35/003* (2013.01); *A61D 7/00* (2013.01)

(58) Field of Classification Search
CPC ....... A61M 35/003; A61M 39/00; A61D 7/00; B65D 2205/02; B65D 11/00
See application file for complete search history.

(56) References Cited

U.S. PATENT DOCUMENTS 6,113,008 A * 9/2000 Arsenault ........... A61M 35/003
                                                            239/337
2003/0032980 A1* 2/2003 Stenton ............ A61B 17/00491
                                                            606/213

(Continued)

FOREIGN PATENT DOCUMENTS

KR    2013 0095217 A    8/2013
WO    2010/051218 A1    5/2010

OTHER PUBLICATIONS

International Search Report, PCT/IB2015/001700, dated Dec. 8, 2015 (2 pages).

*Primary Examiner* — Catherine L Anderson
*Assistant Examiner* — Arjuna P Chatrathi
(74) *Attorney, Agent, or Firm* — Ware, Fressola, Maguire & Barber LLP

(57) ABSTRACT

An applicator for external action formulations is shown, and in particular a disposable applicator for formulations combatting ectoparasites of humans and animals is shown, including at least one formulation container (2) provided with a dispensing outlet (21). In order to protect the patient against possible injury during the application of the formulation, the applicator (1) also includes a plastic cap (3) having a form of a convex solid shell provided with a domed tip end (31) with a dispensing opening (32) which in the working mode of the applicator (1w) surrounds the dispensing outlet (21) of the formulation container (2), and connecting means (23, 34) which in the working mode of the applicator (1w) secure the cap (3) on the formulation container (2).

8 Claims, 2 Drawing Sheets

(56) References Cited

U.S. PATENT DOCUMENTS

| | | | | |
|---|---|---|---|---|
| 2004/0094449 | A1* | 5/2004 | Schmid | A61J 1/067 |
| | | | | 206/524.1 |
| 2006/0011666 | A1* | 1/2006 | Wurtz | B65D 1/095 |
| | | | | 222/541.1 |
| 2006/0065677 | A1* | 3/2006 | Py | A45D 34/04 |
| | | | | 222/383.1 |
| 2006/0269355 | A1* | 11/2006 | Kaufman | A61M 35/003 |
| | | | | 401/207 |
| 2007/0196159 | A1* | 8/2007 | Sogaro | A61M 35/003 |
| | | | | 401/186 |
| 2008/0245314 | A1* | 10/2008 | Brodowski | A01N 25/34 |
| | | | | 119/651 |
| 2008/0304898 | A1* | 12/2008 | Fontana | A45D 34/042 |
| | | | | 401/134 |
| 2010/0087790 | A1* | 4/2010 | Hurwitz | A01K 13/003 |
| | | | | 604/310 |
| 2015/0014322 | A1 | 1/2015 | Kim | |

* cited by examiner

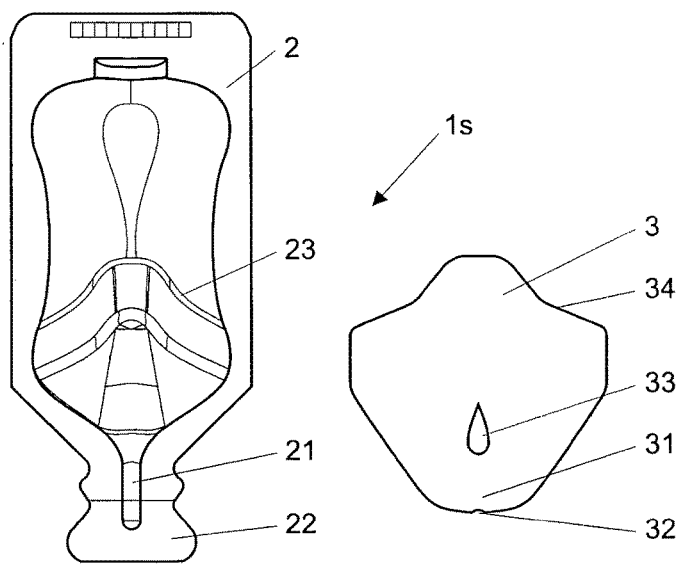
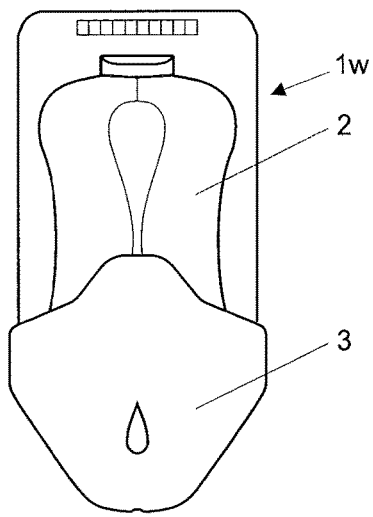
Fig. 1
Fig. 2
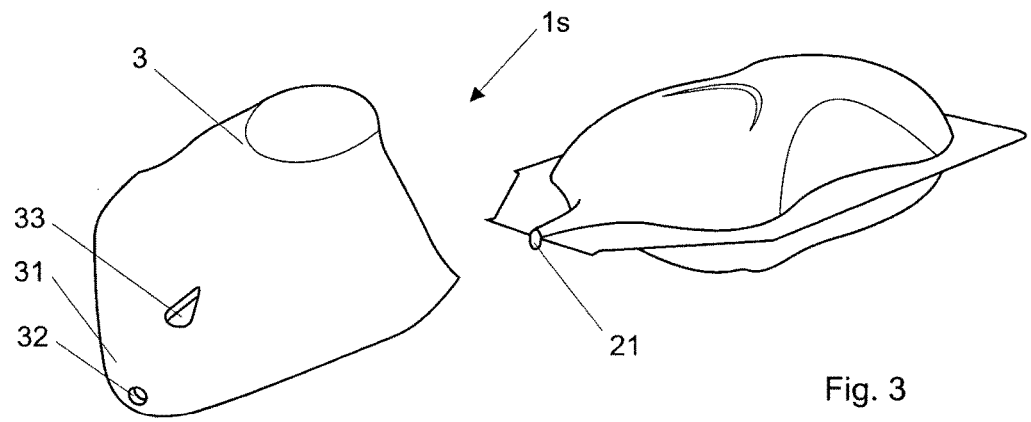
Fig. 3
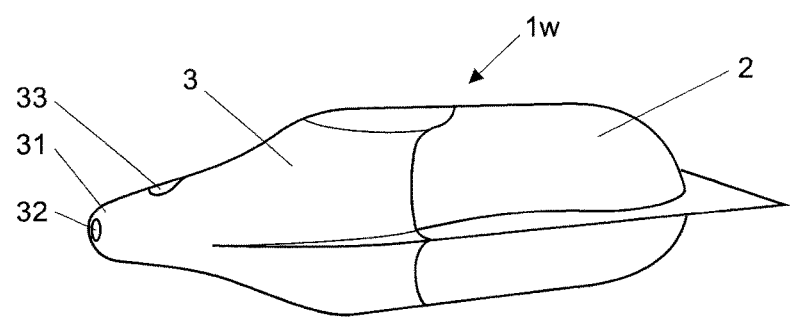
Fig. 4

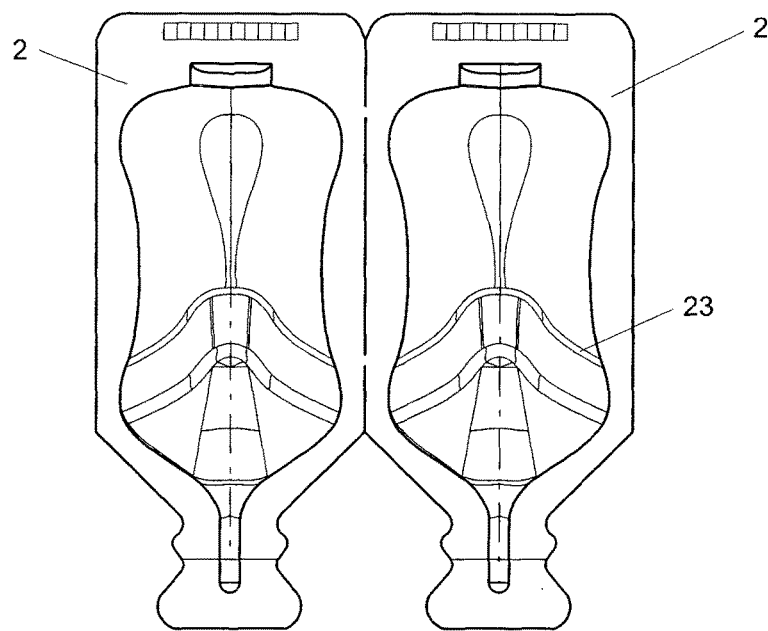
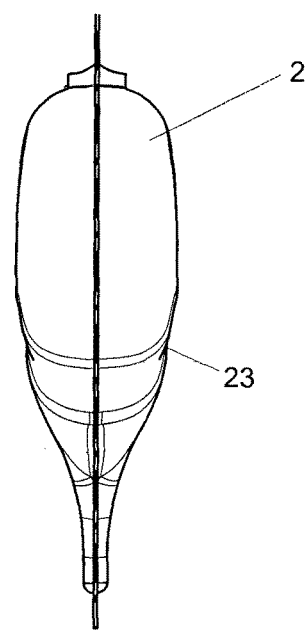
Fig. 5a    Fig. 5b
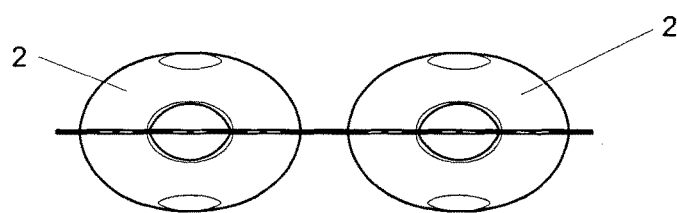
Fig. 5c

APPLICATOR FOR EXTERNAL ACTION FORMULATIONS, IN PARTICULAR A DISPOSABLE APPLICATOR FOR FORMULATIONS COMBATTING ECTOPARASITES

BACKGROUND

The invention relates to an applicator for external action formulations, and in particular to a disposable applicator for formulations combatting ectoparasites of humans and animals, including head lice, fleas, ticks, and the like.

Many formulations to combat ectoparasites are known in the prior art. They are usually applied in several spots on the surface of the skin of the patient, from where they melt over a larger surface, in order to deter or neutralize ectoparasites, for example in a physical way by their immobilization and/or strangulation or in a biocidal way.

These formulations are usually applied directly from the container in which they are stored, or with the use of special applicators. U.S. Pat. No. 5,626,859 discloses such an applicator for applying the composition against ectoparasites in animals having the form of a molded stick, wherein the composition is rubbed on the fur of the animal.

SUMMARY

The aim of the present invention has been to provide an applicator for external action formulations for use in human and veterinary medicine, that would protect the patient against possible injury during the application of the formulation, that would provide easy and even distribution of the formulation while at the same time would be simple, aesthetic and economical in mass production.

The invention provides an applicator for external action formulations, as mentioned in the outset, comprising at least one formulation container provided with a dispensing outlet, characterized in that it further comprises a plastic cap having a form of a convex solid shell provided with a domed tip end with a dispensing opening which in the working mode of the applicator surrounds the dispensing outlet of the formulation container, and connecting means which in the working mode of the applicator secure the cap on the formulation container.

The applicator of the invention is aesthetic and economical to manufacture and with the use of the cap it protects the patient against possible injury, as well provides an easy and even distribution of the formulation.

The cap is preferably further provided with at least one vent hole on the side surface thereof.

The vent hole defines a vent channel between the inner surface of the cap and the outer surface of the container around the dispensing outlet. The venting channel may obviously be defined alternatively or additionally by a groove on said the surface of the formulation container.

Preferably the dispensing outlet of the formulation container is terminated with a snap-off or cut off hermetic closure.

The formulation container and the cap are preferably provided with retaining or snap connecting means matching each other which enable to easily connect and secure the cap on the container by means of resistance (push-fit) or snap fit.

The outer edge of the cap is preferably fitted to the outer surface of the formulation container improving the aesthetics of the applicator in the working mode.

The formulation container has preferably the form of a two-part molding. Such a form is particularly advantageous in mass production.

The formulation containers are preferably connected with each other, in particular in a snap-off or cut-off manner. Thanks to an adequate and specific amount of doses may be stored together without any concern about their loss.

The cap is preferably made of an elastomer, preferably polypropylene elastomer. Material of this type provides an excellent gentleness of contact with the patient's skin during the application of the formulation, as well as good resistance adhering to the formulation container.

BRIEF DESCRIPTION OF THE DRAWINGS

The invention has been presented below in exemplary embodiments and in reference to the drawings, in which:

FIG. 1 schematically illustrates the applicator in the standby mode in top view;

FIG. 2 schematically illustrates the applicator shown in FIG. 1 in the working mode in top view;

FIG. 3 shows the applicator in the standby mode in axonometric view,

FIG. 4 shows the applicator as shown in FIG. 3 in the working mode in axonometric view, and FIG. 5 shows a set of formulation containers in the standby mode in top (FIG. 5a), side (FIG. 5b) and back (FIG. 5c) view.

DETAILED DESCRIPTION

Numerical references to the same functional elements are the same throughout the drawings. Where appropriate, they are supplemented with additional suffixes (a, b, c, d) to differentiate elements of the same functionality but different construction.

The applicator 1s shown in FIG. 1 and FIG. 3 in the standby mode comprises a formulation container 2 and a dispensing cap 3. In this embodiment, the formulation container 2 has a form of a two-part molding, into which in an airtight manner during the manufacturing process a specific dose of formulation for the control of ectoparasites, such as for example spot-on pesticide composition disclosed in U.S. 2012/0029025 A1 or liquid spreading composition with ectoparasiticidal activity disclosed by the applicant in the international application PCT/PL2014/000090, has been introduced.

The formulation container 2 is equipped with a capillary dispensing outlet 21, which in the applicator standby mode is terminated with hermetic closure 22.

As shown in FIG. 2 and FIG. 4 after breaking off or cutting off the closure 22 with scissors the formulation contained in the container 2 may leak out from the container 2 in a controlled manner while applying pressure on the walls of the container 2. In order to prevent scratching or wounding the patient's skin by sharp edges of the dispensing outlet 21, before the treatment an elastomeric cap 3 is attached on the formulation container 2 so as to reach the working mode of the applicator 1w.

The cap 3 has a form of convex solid shell made of polypropylene elastomer Sarlink® 3160 (Teknor Apex Company, USA), and having a domed tip end 31 with a dispensing, opening 32. In the working mode of the applicator 1w the domed tip end 31 surrounds the dispensing outlet 21 of the container 2. Additionally, the cap 3 is provided on its side surface with a vent hole 33 which forms a venting channel between the inner surface of the cap 3 and the outer surface of the container 2 in the vicinity of the dispensing outlet 21.

Domed tip end 31 of the cap 3 not only protects the patient from possible injury of the skin already irritated by the presence of the parasite, but also provides easy and even distribution of product.

FIG. 5 shows an exemplary set of formulation containers in standby mode, which comprises a plurality of formulation containers 2 having side edges connected with each other in a snap-off or cut-off manner.

In the embodiment shown in FIG. 1, FIG. 2 and FIG. 5 connecting means of the applicator 1 are profiled recesses 23 formed in the sidewalls of formulation containers 2, with which they can snap inner projections formed on the edge 34 of the cap 3 to transform the applicator to its working mode 1*w*. In the embodiment shown in FIG. 3 and FIG. 4 the edge 34 of the cap 3 has a certain interference fit to the outer surface of the formulation container 2 allowing it to abut to the container 2. In both embodiments, the edge of the cap 34 is fitted to the outer surface of the formulation container 2.

The disclosed embodiments should not be regarded as exhaustive, and some details of the drawing are shown only schematically in order to better illustrate the invention, the essence of which has been characterized in the claims.

The invention claimed is:

1. An applicator for external action formulations, and in particular to a disposable applicator for formulations combatting ectoparasites of humans and animals, comprising
   a formulation container (2) provided with a capillary dispensing outlet (21),
   a plastic cap (3) having a form of a convex solid shell provided with a domed tip end (31) with a dispensing opening (32) that in a working mode of the applicator (1*w*) surrounds the capillary dispensing outlet (21) of the formulation container (2), wherein said dispensing outlet (21) of the formulation container (2) is terminated with a snap-off or cut off hermetic closure (22) and said formulation container (2) has the form of a two-part molding having side edges,
   wherein the formulation container (2) and the cap (3) are provided with retaining or snap connecting means (23, 34) matching each other that, in the working mode of the applicator (1*w*) secure the cap (3) on the formulation container (2) so as to connect and secure the cap on the container by means of at least one of a push fit, a snap fit, and an interference fit, and
   wherein in a standby mode the formulation container is connected to one or more formulation containers (2) that are connected with each other in a snap-off or cut-off manner.

2. The applicator according to claim 1, wherein the plastic cap (3) is further provided with at least one vent hole (33) on a side surface thereof.

3. The applicator according to claim 1, wherein an outer edge (34) of the cap (3) is fitted to an outer surface of the formulation container (2).

4. The applicator of claim 1, wherein there is a space formed between an inner surface of the convex solid shell of the cap (3) and the outer surface of the container (2), wherein an amount of the formulation is stored before dispensing through the outlet (21) so as to provide for a uniform distribution of the formulation.

5. The applicator of claim 1, wherein before the cap is connected and secured on the formation container in the working mode, the formulation container is separated from the one or more formulation containers (2) in the standby mode so as to enable the matching of the formulation container and the cap in the working mode.

6. The applicator according to claim 4, wherein the cap (3) is further provided with at least one vent hole (33) on a side surface thereof.

7. The applicator according to claim 1, wherein the domed tip end (31) of the plastic cap (3) is a convex solid shell made of an elastomer to cover any sharp edges of the dispensing outlet of the formulation container after the hermetic closure (21) is snapped off or cut off and the cap is connected and secured on the formulation container so that in the working mode irritation or injury to human or animal skin of a patient is avoided during application of the formulation when the domed tip end is applied directly to the skin.

8. An applicator for external action formulations, and in particular to a disposable applicator for formulations combatting ectoparasites of humans and animals, comprising
   a formulation container (2) provided with a capillary dispensing outlet (21),
   a plastic cap (3) having a form of a convex solid shell provided with a domed tip end (31) with a dispensing opening (32) that in a working mode of the applicator (1*w*) surrounds the capillary dispensing outlet (21) of the formulation container (2), wherein said dispensing outlet (21) of the formulation container (2) is terminated with a snap-off or cut off hermetic closure (22) and said formulation container (2) has the form of a two-part molding having side edges,
   wherein the formulation container (2) and the cap (3) are provided with retaining or snap connecting means (23, 34) matching each other that, in the working mode of the applicator (1*w*) secure the cap (3) on the formulation container (2) so as to connect and secure the cap on the container by means of at least one of a push fit, a snap fit, and an interference fit,
   wherein in a standby mode the formulation container is connected to one or more formulation containers (2) that are connected with each other in a snap-off or cut-off manner,
   wherein an outer edge (34) of the cap (3) is fitted to an outer surface of the formulation container (2),
   wherein there is a space formed between an inner surface of the convex solid shell of the cap (3) and the outer surface of the container (2), wherein an amount of the formulation is stored before dispensing through the outlet (21) so as to provide for a uniform distribution of the formulation,
   wherein the plastic cap (3) is further provided with at least one vent hole (33) on a side surface thereof, and
   wherein the plastic cap (3) is made of an elastomer.

\* \* \* \* \*